US008697150B2

(12) United States Patent
Ekanayake et al.

(10) Patent No.: US 8,697,150 B2
(45) Date of Patent: Apr. 15, 2014

(54) PROCESS OF EXTRACTING ISOTHIOCYANATES

(75) Inventors: Athula Ekanayake, Cincinnati, OH (US); Scott Alan Vandiest, Cincinnati, OH (US); Jeffrey John Kester, West Chester, OH (US); Paul Henry Zoutendam, Mason, OH (US); Jairus R. D. David, Omaha, NE (US)

(73) Assignee: The Procter & Gamble Company, Cincinnati, OH (US)

(*) Notice: Subject to any disclaimer, the term of this patent is extended or adjusted under 35 U.S.C. 154(b) by 261 days.

(21) Appl. No.: 12/750,999

(22) Filed: Mar. 31, 2010

(65) Prior Publication Data

US 2011/0245526 A1    Oct. 6, 2011

(51) Int. Cl.
A61K 36/31        (2006.01)
A01N 65/00        (2009.01)

(52) U.S. Cl.
USPC ........................................................ 424/755

(58) Field of Classification Search
USPC ........................................................ 424/755
See application file for complete search history.

(56) References Cited

U.S. PATENT DOCUMENTS

| | | | |
|---|---|---|---|
| 6,361,812 B1 | 3/2002 | Ekanayake et al. | |
| 6,558,723 B2 | 5/2003 | Ekanayake et al. | |
| 6,824,796 B2* | 11/2004 | Pusateri et al. | 424/755 |
| 7,105,190 B2 | 9/2006 | Ekanayake et al. | |
| 7,658,961 B2 | 2/2010 | Ekanayake et al. | |
| 2003/0064131 A1 | 4/2003 | Murata et al. | |
| 2003/0235634 A1 | 12/2003 | Pusateri et al. | |
| 2005/0031768 A1* | 2/2005 | Sakai et al. | 426/629 |
| 2005/0079255 A1 | 4/2005 | Ekanayake et al. | |
| 2006/0127996 A1 | 6/2006 | Fahey | |
| 2008/0193615 A1 | 8/2008 | Cirigliano et al. | |

FOREIGN PATENT DOCUMENTS

| | | |
|---|---|---|
| DE | 2046756 | 3/1972 |
| DE | 10 2005 03361 A1 | 1/2007 |
| GB | 224524 | 8/1925 |
| WO | WO 2006/065736 A2 | 6/2006 |

OTHER PUBLICATIONS

Vaughn et al. (Indust. Crops and Products, v. 21 (2005), p. 193-202).*
Wilkinson et al. (J. Sci. Food Agric., v. 35 (1984), p. 543-552).*
Szakacs-Dobozi et al. (Appl. Microbiol. Biotechnol., (1988) 29: 39-43).*
Steven F. Vaughn and Mark A. Berhow, "Glucosinolate Hydrolysis Products from Various Plant Sources: pH Effects, Isolation, and Purification"—New Crops and Processing Technology Research, Agricultural Research Service—USDA, Dated Mar. 25, 2004.
Vladimir Borek and Matthew J. Morra, "Ionic Thiocyanate (SCN) Production from 4-Hydroxybenzyl Glucosinolate Contained in Sinapis alba Seed Meal"—J. Agric. Food Chem., 2005, 53 Publication Date Sep. 24, 2005.
Andrew P Wilkinson et al, "Myrosinase Activity of Cruciferous Vegetables", Journal of the Science of Food and Agriculture, vol. 35, No. 5, 1984, pp. 543-552, XP000002656694, ISSN: 0022-5142.
A Ekanayake et al, "Isogard™ A Natural Anti-Microbial Agent Derived from White Mustard Seed", proceeding of the $1^{st}$ International Symposium on natural preservatives in food systems: Princeton, US, Mar. 30-31, 2005, International Society for Horticultural Science, US, vol. 709, Mar. 30, 2005, pp. 101-108 XP009147485, ISBN: 90-6605-509-X.
A Ekanayake et al, "Isogard™: A natural preservative derived from white mustard seeds", 2004 IFT Annual Meeting, Jul. 12-16 Las Vegas NV. Jul. 15, 2004, pp. 1-1, XP00263074, http://ift,confex,com/ift/2004/techprogram/paper_26555.htm.
PCT International Search Report dated Aug. 11, 2011—9 pgs.
Anonymous: "Mustard", Minn-Dak Growers, Ltd, Jun. 20, 2009, XP002634075, Retrieved from the Internet: URLhttp://www.minndak.com/Mustard.htm.
Tyagi et al.: "Effect of Mustard Flour Incorporation on Nutritional, Textural and Organoleptic Characteristics of Biscuits," Journal of Food Engineering, vol. 80, No. 4, Jan. 18, 2007, pp. 1043-1050, XP005834548.
Anonymous: New Products & Technologies: "Innovations in Food Safety", 2004 IFT Annual Meeting, Jul. 12-16—Las Vegas, NV; Retrieved from the Internet: http://ift.confex.com/ift/2004/techprogram/session3278_htm; Jul. 12, 2004.
U.S. Appl. No. 12/751,015, filed Mar. 31, 2010, Ekanayake et al.

* cited by examiner

Primary Examiner — Robert Havlin
(74) Attorney, Agent, or Firm — Amy M. Foust; Kelly McDow; David Kent Mattheis

(57) ABSTRACT

A process for producing an essential oil. The essential oil can be white mustard essential oil. The white mustard essential oil can include a moisture sensitive isothiocyanate compound. The moisture sensitive isothiocyanate compound can be 4-HBITC. The essential oil can be produced from mustard seed, which can comprise a precursor sinalbin and myrosinase enzyme. The mustard seed can be reduced into a powder. Activation of the myrosinase enzyme by using a water solvent and a promoter to form a slurry can be performed, wherein the myrosinase enzyme catalyzes the production of an essential oil comprising an isothiocyanate from the sinalbin precursor.

1 Claim, No Drawings

PROCESS OF EXTRACTING ISOTHIOCYANATES

FIELD

Embodiments of the present invention relate to processes of extracting isothiocyanates from plant materials. More particularly, but not exclusively, embodiments of the present invention relate to processes of extracting essential moisture sensitive isothiocyanates from mustard seeds and essential oils of mustard seeds.

BACKGROUND

Consumer products can provide a hospitable environment for rapid microbial growth. Such exposure can, and frequently does, result from inadvertent microbial inoculation of the product during manufacturing or packaging. Spoilage microorganisms, for example in food products, can then rapidly proliferate by feeding on nutrients provided by the product.

Preservatives, such as sorbates, benzoates, organic acids, and combinations thereof have been used in various products, particularly foods and beverages, to provide some degree of microbial inhibition. However at levels effective to inhibit microbial growth, some of these preservatives can contribute off-flavors in the product, thus making the product undesirable for its intended purpose. Similarly, natural preservatives, such as natamycin, are frequently used in food and beverage products to inhibit microbial growth. Unfortunately, while these natural preservatives may be effective against either yeast or bacteria, they may not be effective against both.

It has been disclosed that the essential oil of mustard plants, which contain isothiocyanates, exhibits an antibacterial and antimycotic effect in oral therapies and on certain foods. See e.g., Sekiyama et al., U.S. Pat. No. 5,334,373, assigned to Nippon Sanso Corp., issued Aug. 2, 1994; and Madaus et al., U.S. Pat. No. 3,998,964, issued Dec. 21, 1976. The isothiocyanate compounds in mustard essential oils are the active agents that provide the antimicrobial effect. The essential oil derived from white or yellow mustard plants (*Sinapis alba* or *Brassica alba*), also provides the foregoing antibacterial and antimycotic benefits. Additionally, isothiocyanate compounds are effective antimicrobial agents at relatively low usage levels. The principal isothiocyanate present in the white mustard essential oil, 4-hydroxybenzyl isothiocyanate (4-HBITC), is a moisture sensitive compound that begins to degrade (i.e. hydrolyze) within hours of being exposed to moisture. When degraded, the 4-hydroxybenzyl isothiocyanate forms, among other compounds, 4-hydroxybenzyl alcohol.

However, the isolation and extraction of white mustard essential oils from mustard plants presents problems. Unlike most of the other plant essential oils that are volatile and can be steam distilled, white mustard essential oil is not volatile at atmospheric pressure and requires that it be extracted out of the seeds by the use of a solvent or a method such as supercritical fluid extraction. Additionally white mustard essential oil, unlike most of the other plant essential oils, is relatively unstable, especially so when exposed to moisture. This instability imposes the additional condition that when the essential oil is generated that it be extracted from the mustard seed and soon stabilized thereafter to maintain its antimicrobial properties.

Currently, the mustard processing industry makes use of the white mustard flour primarily while the essential oil is largely ignored. In fact, to make use of the white mustard flour without the "heating" sensation of mustard, the ground mustard flour is subjected to a thermal deactivation step. Here, the enzyme myrosinase, which catalyzes the formation of 4-hydroxybenzyl isothiocyanate from its precursor 4-hydroxybenzylglucosinolate, also known as sinalbin, is intentionally deactivated so that the essential oil does not form when the flour is mixed with moist food products such as meat and sausage. Additionally, because of its instability, 4-hydroxybenzyl isothiocyanate is not currently available commercially, whether as a natural product or as a pure chemical.

Accordingly, white mustard essential oil has not been widely known or widely utilized in the art for its antibacterial and antimycotic effect. However, the present inventors have surprisingly discovered that, in one embodiment, by generating the white mustard essential oil by adding water to defatted ground mustard seed, extracting the white mustard essential oil using solvents or supercritical fluids, drying the essential oil by removing the solvent and residual moisture, and then intimately blending the resulting white mustard essential oil with a hygroscopic carrier, the moisture sensitive isothiocyanate compounds contained therein can be stabilized. Hence, the blend of white mustard essential oil with a hygroscopic carrier is, thereafter, capable of being used as an effective antibacterial and antimycotic agent for solid food products. The scaling up issues involved in making white mustard essential oil on a larger scale and instability of white mustard essential oil has not been recognized by others involved in extracting essential oils. For example, some of the publications involved describe a first solvent extraction step to remove the fixed or triglyceride component of mustard oil followed by de-solventizing the defatted mustard seed prior to activation with water to generate the active component 4-hydroxybenzyl isothiocyanate.

Other earlier attempts to make WMEO comprised of the following steps as described in the referenced art. First solvent extracting the ground mustard seed to remove all of the fixed oils, drying the seed, wetting with water and allowing the 4-HBITC generating reaction to proceed for up to 24 hours, extracting the moistened mustard seed residue with acetone, removing the acetone under reduced pressure and extracting the residue with 96% ethanol to yield a solution of the active component 4-HBITC as described in DE2046756A. GB 224524 describes solvent extracting or pressing out the fixed oil from mustard seed and then adding water to create a pasty mass that is allowed to react for 24 to 48 hours in order that the sinalbin precursor is converted to sinalbin mustard oil. After pressing this pasty mass to remove water, myrosinase, sinapic bisulfate, sugar, and traces of 4-HBITC, the residue as well as the pressed extract is solvent extracted with diethyl ether and the ether removed under reduced pressure to yield sinalbin oil. U.S. Pat. No. 6,824,796 describes a process for extracting the isothiocyanates from leafy vegetables and roots such as horseradish. Here vegetable oil is used as the solvent for the isothiocyanates after activation of the myrosinase catalyst by grinding the plant material in water. The scientific literature also describes methods based on first de-fatting mustard seed using solvents, then drying the seed to rid it of any residual solvents, crushing the de-fatted seed in water and allowing the reaction to proceed for about 24 hours in the presence of a solvent (Borek, V. & Morra, M. J. 2005. Ionic thiocyanate production from 4-hydroxybenzyl glucosinolate contained in *Sinapis alba* meal. Journal of Agricultural and Food Chemistry, 53, 8650-8654. Vaughn, S. V. and Berhow, M. A. 2005. Glucosinolate hydrolysis products from various plant sources: pH effects, isolation and purification. Industrial Crops and Products, 21, 193-202.). In all of these instances the full potential of the myrosinase system has not been utilized and moreover as a result the time & other logistics of the extraction process do not provide viable conditions to make the essential oil of white mustard seed in any industrial sized quantity in an economical manner.

Some of the procedures above add a very high cost to the overall process and the additional burden of dealing with another solvent removal and evaporation step. Some others do not attempt to accelerate the reaction by the addition of known activators of the myrosinase enzyme such as ascorbic acid thus making a large scale process very inefficient and time consuming. Process efficiencies that can be realized by using the proper ratio of partially defatted mustard seed, water, and ethyl acetate that allows a low speed centrifugation step to separate the solvent containing the white mustard essential oil have also not been revealed in the literature.

SUMMARY

One embodiments relates to a process for producing an essential oil. It can include providing a plant material comprising a glucosinolate precursor and myrosinase enzyme, wherein the plant material comprises a fixed oil; reducing the particle size of the plant material to produce a powder; activating the myrosinase enzyme by using a water solvent and a promoter to form a slurry, wherein the myrosinase enzyme catalyzes the production of an essential oil comprising an isothiocyanate from the glucosinolate precursor; and separating the slurry into an essential oil and a residual solvent.

Another embodiment relates to a process for producing an essential oil. It can include providing mustard seed comprising a precursor sinalbin and myrosinase enzyme, wherein the mustard seed comprises a fixed oil; optionally, reducing the fixed oil content of the mustard seed; reducing the particle size of the seed to produce a mustard powder; activating the myrosinase enzyme by using a water solvent and a promoter to form a slurry, wherein the myrosinase enzyme catalyzes the production of an essential oil comprising an isothiocyanate from the sinalbin precursor; and separating the slurry into an essential oil and a residual solvent. The essential oil can be a white mustard essential oil, which can include a moisture sensitive isothiocyanate compound, which can be 4-hydroxybenzyl isothiocyanate.

DETAILED DESCRIPTION

I. Definitions

All percentages, ratios, and proportions used herein are by weight unless otherwise specified.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

All lists of items, such as, for example, lists of ingredients, are intended to and should be interpreted as Markush groups. Thus, all lists can be read and interpreted as items "selected from the group consisting of" . . . list of items . . . "and combinations and mixtures thereof."

Referenced herein are trade names for components including various ingredients utilized in the present invention. The inventors herein do not intend to be limited by materials under a certain trade name. Equivalent materials (e.g., those obtained from a different source under a different name or reference number) to those referenced by trade name may be substituted and utilized in the descriptions herein.

The compositions and processes herein may comprise, consist essentially of, or consist of any of the features or embodiments as described herein.

In the description of the various embodiments of the present disclosure, various embodiments or individual features are disclosed. As will be apparent to the ordinarily skilled practitioner, all combinations of such embodiments and features are possible and can result in preferred executions of the present disclosure. While various embodiments and individual features of the present invention have been illustrated and described, various other changes and modifications can be made without departing from the spirit and scope of the invention. As will also be apparent, all combinations of the embodiments and features taught in the foregoing disclosure are possible and can result in preferred executions of the invention.

As used herein, the articles including "the", "a", and "an", when used in a claim or in the specification, are understood to mean one or more of what is claimed or described.

As used herein, the terms "include", "includes", and "including" are meant to be non-limiting.

As used herein, the term "plurality" means more than one.

As used herein, the term "antimicrobial effect" means that the product inhibits growth of, eliminates, and/or otherwise decreases the presence of microorganisms such as, for example, yeast, bacteria, mold, and/or fungus, preferably yeast and/or bacteria.

As used herein, "essential oil" refers to the set of all the compounds that can be distilled or extracted from the plant from which the oil is derived and that contributes to the characteristic aroma of that plant. See e.g., H. McGee, On Food and Cooking, Charles Scribner's Sons, p. 154-157 (1984). In accordance with embodiments of the present invention, the essential oil preferably originates from the white or yellow mustard plant (*Sinapis alba* or *Brassica alba*), which is capable of producing a moisture sensitive isothiocyanate compound, and more specifically, 4-hydroxybenzyl isothiocyanate (4-HBITC).

As used herein, the term "moisture sensitive" means that the isothiocyanate compound degrades in the presence of water. This degradation proceeds via a hydrolysis reaction, thereby leading to a reduction in level of the active isothiocyanate antimicrobial agent with time of storage in the presence of water. The method for determining moisture sensitivity is set forth in the Test Method section below. Moisture sensitive isothiocyanates are characterized by a reduction in concentration of the isothiocyanate compound of at least about 20% of the starting concentration, when suspended in an aqueous phosphate buffer having a pH of about 3.6, and a temperature of from about 20° C. to about 23° C., over a 24 hour period. One example of a moisture sensitive compound is 4-hydroxybenzyl isothiocyanate.

As used herein, the term "natural component," with reference to the corresponding essential oil, refers to a component utilized in the present invention that is obtained from the naturally occurring essential oil.

As used herein, the term "substantially free of" means comprise less than about 0.05% by weight (i.e. less than about 500 parts per million).

II. Embodiments of the Process

Embodiments of the present invention relate to processes of extracting isothiocyanates from plant materials. In one respect, embodiments of the present invention relate to processes of extracting oils from plants. Embodiments of the present invention relate to processes of extracting essential moisture sensitive isothiocyanates from mustard seeds and essential oils of mustard seeds.

A. The Isothiocyanate Compound

In accordance with embodiments of the present invention, the process comprises extracting essential oils from plants. Such oils can include white mustard essential oil (WMEO). Such white mustard essential oils can include isothiocyanate compounds, which can be a moisture sensitive compound. Thus, embodiments disclosed herein can include extracting a moisture sensitive isothiocyanate compound (i.e., a compound bearing a —N=C=S moiety), such as, for example, the compound 4-hydroxybenzyl isothiocyanate, from white mustard essential oil derived from mustard plants. Such compounds have been previously identified as having beneficial antimicrobial activity in food products. See U.S. Pat. No. 7,658,961, assigned to The Procter & Gamble Company. As is known, these compounds are often used in combination with the known preservatives benzoic acid, sorbic acid, or salts thereof and/or the moisture sensitive isothiocyanate compound, such as the 4-hydroxybenzyl isothiocyanate in white mustard essential oil, can be combined with a hygroscopic carrier that attracts, absorbs, and binds moisture, without the use of these known preservatives.

Although any moisture sensitive isothiocyanate can be extracted by embodiments of the processes disclosed herein, the extraction of 4-hydroxybenzyl isothiocyanate (4-HBITC) is one specific embodiment thereof. In embodiments of the present invention, the constituent comprising the moisture sensitive isothiocyanate compound can be an essential oil, natural component of an essential oil, or synthetic component of an essential oil (all as described in more detail hereinafter) of the white or yellow mustard family (*Sinapis alba* or *Brassica alba*). As is known, the Brassica family of plants is a small family having about 2000 species and over 300 genera (see e.g. Natural Food Antimicrobial Systems, edited by A. S, Naidu, CRC Press LLC, pp. 399-416, 2000). Alternatively, the constituent comprising the moisture sensitive isothiocyanate compound may be an essential oil, natural component of an essential oil, or synthetic component of an essential oil of any other family of plants which may produce a moisture sensitive isothiocyanate compound. See e.g., Food Chemistry, Edited by O. R. Fennema, Marcel Dekker, Inc., pp. 602-603 (1985) and Naturally Occurring Antimicrobials in Food, Council for Agricultural Science and Technology, pp. 31-32 (1998).

As is known in the art, the seeds and/or flowers of any of, for example, a *Bras sica* species, may be, homogenized, ground, crushed, pressed, or otherwise damaged to activate one or more precursors (e.g., glucosinolates) of the corresponding essential oil. Isothiocyanate compound production from the oil is known to occur by enzyme catalysis upon, for example, homogenizing, grinding, crushing, pressing, or otherwise damaging the plant, seed, and/or flower thereof. See e.g., Concannon, WO 94/01121, published Jan. 20, 1994 and Brown et al., "Glucosinolate-Containing Plant Tissues as Bioherbicides", Journal of Agricultural Food Chemistry, Vol. 43, pp. 3070-3074 (1995). The enzyme commonly known to participate in the production of the isothiocyanate compound upon interaction with a glucosinolate is myrosinase, which is also known as thioglucoside glucohydrolase (and having enzyme classification number EC 3.2.3.1). Myrosinase is known to be non-specific for various glucosinolates.

Accordingly, the embodiments herein can be related to any plant material that comprises a glucosinolate precursor and myrosinase enzyme, one non-limiting example which is mustard seed. In specific embodiments, plant materials containing a moisture sensitive isothiocyanate compound is envisioned. The plant materials can include the family Brassicaceae (previously Cruciferae) and can include mustards (*Brassica nigra, Brassica juncea, Brassica hirta* or *Sinapis alba*), cabbage (*Brassica oleracea*), cauliflower (*B. oleracea* var. *botrytis*), brussel sprouts (*B. oleracea* var. *gemmifera*), broccoli (*B. oleracea* var. *italica*), kohlrabi (*B. oleracea* var. *gongylodes*), wasabi (or Japanese horseradish) (*Wasabia japonica*), canola (*B. napus*) and turnips (*B. rapa*). Additional non-limiting examples include other plant materials such as capers (Capparaceae) and Moringaceae.

B. Extraction Process

Accordingly, embodiments of extracting isothiocyanate compounds of essential oils of mustard plants are disclosed herein. In one embodiment, white mustard essential oil (WMEO) comprising from about 5% to about 35% 4-hydroxybenzyl isothiocyanate (4-HBITC) is provided from white or yellow mustard, *Sinapis alba*. WMEO comprising from about 10% to about 30% 4-hydroxybenzyl isothiocyanate (4-HBITC) can be produced. WMEO comprising from about 15% to about 27% 4-hydroxybenzyl isothiocyanate (4-HBITC) can be produced. WMEO comprising from about 22% to about 28% 4-hydroxybenzyl isothiocyanate (4-HBITC) can be produced. Other embodiments include compositions comprising, however made, white mustard essential oil comprising about 30% to about 35% 4-hydroxybenzyl isothiocyanate (4-HBITC). This active compound in white mustard essential oil, 4-HBITC is a moisture sensitive compound that begins to degrade (i.e. hydrolyze) within hours of being exposed to moisture. Thus, 4-HBITC is very susceptible to hydrolysis at neutral pH. As described, white mustard seeds contain its precursor sinalbin, and the enzyme myrosinase (thioglucosidase glucohydrolase). When activated by the addition of water, producing a moistened mustard seed, myrosinase catalyzes the degradation of sinalbin resulting in 4-hydroxybenzyl isothiocyanate. After a suitable reaction time, the 4-HBITC and other lipid soluble material transfer into the solvent layer and can then be separated from the moistened mustard seed. The solvent can then removed at low temperature under reduced pressure to yield WMEO comprising 4-HBITC. This 4-HBITC preparation, which can be dry, can then be used as the preservative in accordance with U.S. Pat. No. 6,361,812B1; U.S. Pat. No. 6,558,723B2; U.S. Pat. No. 7,105,190B2 and U.S. Pat. No. 7,658,961, all assigned to The Procter & Gamble Company.

The extraction process can comprise the following general steps, all of which are not necessarily required, and all of which are described hereinafter: 1) cold pressing or solvent extracting mustard seeds to remove fixed oil; 2) crushing the reduced fat or fat free mustard seeds to give a defatted white mustard powder; 3) adding the defatted white mustard powder into the solvent and water mixture containing the activator ascorbic acid; 4) letting the myrosinase catalyzed sinalbin hydrolysis reaction happen over a period of time, and allowing the 4-hydroxybenzyl isothiocyanate to dissolve in the solvent; 5) separating the solvent containing 4-hydroxybenzyl isothiocyanate from the moist defatted mustard flour; 6) removing the solvent under reduced pressure to yield white mustard essential oil containing 4-hydroxybenzyl isothiocyanate; and 7) drying the moist defatted mustard flour to yield de-heated and defatted mustard flour.

In one embodiment, white mustard seeds can be first cold pressed to remove as much as possible of the seed oil without increasing the temperature of the press cake. In one embodiment, the press cake temperature can be less than about 70° C. to ensure that myrosinase enzyme activity is retained in the press cake. After milling the press cake, in one embodiment it can be moistened to get myrosinase to be active in catalyzing the hydrolysis of sinalbin to 4-HBITC. In one embodiment, ascorbic acid at about 1 millimole can be used an effective activator of the myrosinase enzyme. A solvent can be mixed in with the reacting moist mustard system, which can ensure that the 4-HBITC produced by the reaction will transfer to the lipophilic ethyl acetate layer when utilizing an ethyl acetate solvent. After a reaction time, in one embodiment of about 4 hours, the ethyl acetate layer can be separated. The press cake:water:ethyl acetate ratio can be about 1:0.3:2 to avoid the formation of a stable emulsion and to have sufficient water to allow the enzyme to be active. The ethyl acetate containing the 4-HBITC and the residual mustard oil can be removed from the reaction system by centrifugation and immediately evaporated under vacuum to yield WMEO. Here, in one embodiment, drying the ethyl acetate can be avoided. The WMEO can then be kept frozen to avoid the degradation of 4-HBITC. However, plating the WMEO on maltodextrin as taught in U.S. Pat. No. 7,658,961 can be performed to allow it to be stored at refrigerated or room temperature.

Embodiments of the extraction processes as described herein are now described in more detail.

i. Reducing Oil Content

In one embodiment, once provided, the fixed oil content of the mustard seed, which can comprise a precursor sinalbin and myrosinase enzyme, can be reduced. The fixed oil content of the mustard seed is about 26% to about 28% by weight. The fixed oil content is comprised of the triglycerides found in the mustard seed. Once reduced, the fixed oil content of the mustard seed can comprise from about 2% to about 10%, or from about 4% to about 9%, or from about 6% to about 8%.

Reducing the oil content can comprise mechanical expression, such as cold pressing or solvent extracting mustard seeds to remove fixed oil followed by crushing the reduced fat or fat free mustard seeds to give a defatted white mustard powder.

In one embodiment, mechanical expression, such as cold pressing, can be used to reduce the fixed oil content. Cold pressing can generally involve subjecting the thing to be cold pressed to temperature and pressure, as is well known in the art. In one embodiment, cold pressing can include subjecting the mustard seed to pressure and temperature as described above and extracting essential oil from the seed without the use of solvent extraction. This embodiment can be termed "oil expressing" and can be without the use of a solvent extraction. Once pressed, as much oil as possible can be removed. In such an embodiment, the temperature can be kept at or below about 70° C., or below about 50° C. Such temperature can leave the myrosinase active. Once the oil is extracted or expressed, the oil and pressed cake that is left after extraction of the oil can be processed as disclosed hereinafter. In one embodiment, the pressed cake can be crushed, milled, or otherwise processed by reducing the particle size into a mustard powder.

As described, the mustard seed can be mechanically expressed, such as by cold pressing. This expressing can produce a pressed mustard seed cake, which includes the essential oil. In general, mustard seed has an oil content of from about 26% to about 28% and a moisture content of form about 6% to about 7%. By cold pressing or crushing the mustard seed, the myrosinase catalyzed hydrolysis reaction of glucosinolate cannot occur because the moisture content is not sufficient to support enzymatic action. Thus, mustard seeds provide a good source for pressing out or expelling the fixed oil. Oil expressing can be done in many different types of machines to produce a defatted powder.

In one embodiment, a single press screw can press mustard seeds within a press cylinder. The single press screw can include a feeding hopper at one end of the screw containing cylinder, a press head at the other end where the seed is pressed to squeeze out the oil, and a perforated section between the hopper and press head. The perforated section can allow the expressed oil to flow out. Pressed mustard seeds result in a defatted press cake that can be extruded or forced through a nozzle in the press head and can form a continuous cylindrical pellet as it exits the machine. The large thermal capacity of these machines can prevent the temperature of the press cake from rising much above about 60° C. to about 65° C., which can be beneficial for pressing mustard seed. At this point, the defatted pressed cake can have about 6-8% residual fat and can also contain the precursor sinalbin and the enzyme myrosinase. In one embodiment, the temperature that the press cake had experienced during the pressing step is insufficient to denature the myrosinase enzyme. The defatted mustard can then exit the press as a cylindrical pellet that can be milled to a fine powder, which can in one embodiment become the raw material for the next step in the process.

In another embodiment, a type of screw press called a cage type of press can be used. In this embodiment, the press cylinder containing the press screw can be slotted from a point close to the feeding hopper to the end of the press cylinder. The press screw can push the mustard seed against these slots to press out the oil, which can exit the press cylinder via the longitudinal slots with some plant debris. The slot spacing and the press screw pressure pieces can be adjusted to give the clearest oil and the defatted press cake with the lowest possible oil content. The long press area generates much friction and consequent heat. The thermal capacity of these types of presses is low and as a result the press cake tends to warm to temperatures as much as about 80° C. to about 85° C. Thus, in some embodiments, the myrosinase activity of the defatted press cake may be adversely affected by this rise in temperature. If the press cake temperature is from about 70° C. to about 75° C. when it exits from the press, it can be cooled soon after thereby maintaining sufficient enzyme activity to catalyze the hydrolysis of sinalbin when the press cake is wetted. The defatted press cake may contain up to 17% residual fat.

Another variation in the use of the cage type of screw press is to divide the mustard seed into two lots. The first of these lots can be pressed so that the press cake temperature does not rise above from about 65° C. to about 70° C. while the second lot can be pressed to maximize oil removal, irrespective of the press cake temperature. In this manner, when the two lots are re-combined after pressing, the final residual oil content can be much lower than 17% and, on wetting, the combined press cake and the myrosinase enzyme in the first lot will be active and able to catalyze the hydrolysis of sinalbin from both lots to 4-hydroxybenzyl isothiocyanate. Depending on the enzyme activity required for the catalysis of the hydrolysis reaction, the proportions of the two lots can be changed. For example, mustard seed can be divided into three lots. Two of these lots can be subjected to the higher temperature pressing step while the third lot can be subjected to the lower temperature pressing step thus preserving the enzyme activity of this third lot. The three lots can be re-combined to give a final residual oil content of much less than 17% and an enzyme activity sufficient to catalyze the hydrolysis of sinalbin of all of the lots to 4-hydroxybenzyl isothiocyanate.

Following reducing the oil content by the processes above, a defatted mustard press cake or powder is provided and is processed further.

ii. Treating with Solvent

The powder or pressed cake can then be treated to extract the residual fixed oil and activate the myrosinase enzyme. Such treatment can be performed by adding a solvent and a promoter. Solvents can include water solvents, ethyl acetate, water, and combinations and mixtures thereof. The solvents can be added with the powder or pressed cake in a reaction vessel to form a reaction mixture.

Once the solvent and the promoter are added, the myrosinase enzyme will be activated, and the mustard cake or powder and solvent and promoter form a slurry. The myrosinase enzyme can catalyze the production of an essential oil comprising an isothiocyanate from the sinalbin precursor. As described herein, the essential oil can be WMEO, and the isothiocyanate can be a moisture sensitive isothiocyanate, such as 4-HBITC.

Solvents that can be used to extract the residual fixed oil of the partially defatted mustard press cake along with the generated 4-hydroxybenzyl isothiocyanate including, but are not limited to, ethyl acetate, hexane, heptanes, methyl pentane, dichloromethane, and chloroform. In one embodiment, ethyl acetate is used. Ethyl acetate is not water soluble and thus can be removed easily from the reaction mixture by a simple centrifugation step. Additionally, ethyl acetate forms a lower boiling azeotrope with water having the composition 91.53% ethyl acetate and 8.47% water with a boiling point of 70.4° C. compared to 77.2° C. for pure ethyl acetate. This formation allows the separated ethyl acetate to be removed from the final solvent removal step without a pre-drying step because the added water is also removed by the azeotrope that it forms with ethyl acetate. Drying agents used to remove water from solvents have to be regenerated before reuse and that requires them to be heated and kept under dry conditions before use. Regeneration of drying agents releases residual solvents in addition to water and such vapors cannot be vented to the atmosphere thus requiring vapor scrubbing and solvent recovery steps that add to complexity and cost. An added benefit of using ethyl acetate as solvent is the azeotrope that ethyl acetate forms with water reduces the boiling point of ethyl acetate by about 7° C. thus allowing a lower temperature of evaporation. The solvent can be mixed with the required amount of water in a reaction tank and the powdered, partially defatted mustard press cake can be added into the tank with mixing to ensure good wetting. In another embodiment, the powdered, partially defatted mustard press cake can be first mixed with the dry activator/promoter to ensure homogeneity and wetted with the requisite amount of water in mixing vessel. The solvent can then be added to this mixing vessel and mixed at high speed first to ensure homogeneity and then mixed at lower speed to maintain the slurry in suspension for the reaction to take place and the 4-hydroxybenzyl isothiocyanate to transfer to the solvent.

In other embodiments, a combination of ethyl acetate and water can be used. The particular amounts of the ethyl acetate and water can be varied. In embodiments using partially defatted mustard press cake, the fat of the defatted mustard press cake content can be relevant to the amount of solvent used. In one embodiment, the defatted mustard pressed cake can have as high as 17% fat content. In such an embodiment, the added water can be maintained at less than about 40% with a maximum ethyl acetate content of about 2 times the weight of the partially defatted mustard press cake used to form a mustard slurry. Such an embodiment can avoid the formation of a stable emulsion. In one embodiment, emulsion formation can be avoided in order to be able to separate the ethyl acetate from the reaction mixture by a simple centrifugation step described hereinafter. Thus, in one embodiment, the proper amount of moisture controls such that the reaction begins and partition between the ethyl acetate and the white mustard powder but not too much to form an emulsion.

Additionally, the defatted white mustard:water:ethyl acetate ratio is selected to provide sufficient water for the myrosinase catalyzed hydrolysis reaction of sinalbin to 4-hydroxybenzyl isothiocyanate to occur efficiently and also to avoid forming a stable emulsion described above when the moistened defatted mustard press cake is mixed with ethyl acetate.

Accordingly, in one embodiment, the ratio of PDMS:water:ethyl acetate can be about 1:0.4:1.8. Thus, in one embodiment, the ratio of defatted mustard press cake to water to ethyl acetate can be 1 part defatted mustard press cake: 0.4 part water: 1.8 parts ethyl acetate, on a weight basis. In another embodiment, the ratio of PDMS:water:ethyl acetate can be about 1:0.25:1.5 to about 1:0.5:3, by weight.

A promoter can also be used. A promoter is a substance that speeds up the reaction catalyzed by the myrosinase enzyme. In one embodiment, the promoter can be ascorbic acid. In other embodiments, metal salts could be used. The promoters can be added at between about 0.75 millimole and about 3 millimoles, or about 1.0 millimole and about 2.5 millimoles, 1.5 millimole and about 2.0 millimoles, or about 1.0 millimole. The amount of promoter used allows for the proper activation of the myrosinase enzyme. Lower amounts may not provide for the proper activation of myrosinase enzyme while higher amounts may react with 4-HBITC to give compounds called ascorbinogens, which may reducing the yield of 4-HBITC.

These promoters can be used for the following reasons. Myrosinase or thioglucosidase glucohydrolase (E.C. 3.2.1.147) is an enzyme with a site or sites that can host the promoters, such as the ascorbic acid molecule. The addition of ascorbic acid at low concentrations, such as those disclosed herein, for example, about 1 mM, allows for the reaction rate to proceed advantageously from a process feasibility viewpoint. In the absence of the activator, the maximum concentration of 4-HBITC in the solvent occurs after about 24 hours in the reaction slurry comprising partially defatted white mustard, water and solvent at room temperature of about 21° C. Upon addition of a promoter, such as ascorbic acid, the maximum concentration in a similar reaction system is reached within about 3-4 hours and that concentration is maintained for the next 20-22 hours providing a wide enough window to centrifuge and separate the water immiscible organic solvent in large scale production systems.

In one embodiment, the partially defatted mustard seed (PDMS) can be directly added to the solvent mixture to form a slurry. By adding partially defatted mustard seed directly to the solvent, such as an ethyl acetate-water mixture, in a reacting vessel followed by the addition of a promoter, the process can be sped up by avoiding a cumbersome pre-wetting step. PDMS when wetted with water tends to form lumps in contrast to adding to an ethyl acetate-water mixture when the PDMS wets easily and disperses easily to form a slurry that is stirred easily.

The slurry can be allowed to react for a specified reaction time. In one embodiment, the reaction time can be about 4 hours. In another embodiment, the reaction time can be up to about 4 hours. In another embodiment, the reaction time can be from about 3 to about 5 hours. In another embodiment, the reaction time can be from about 2 to about 6 hours. In another embodiment, the reaction time can be from about 1 to about 8 hours. In another embodiment, the reaction time can be at least about 1 hour.

Additionally, in one embodiment, the addition of cellulase type enzymes to the PDMS can also increase the yield of 4-HBITC during this reaction phase.

iii. Separation

Further, a separation step can then be performed. The separation step can be performed to separate the solvent from the reaction mixture such that the slurry is separated into a filter cake, an essential oil, and a residual solvent, wherein the essential oil and residual solvent can be an essential oil enriched solvent that is then separated into an essential oil and a residual solvent.

After the hydrolysis reaction above to generate 4-HBITC is complete, the slurry can be separated. In one embodiment, the slurry can be separated into a filter cake, an essential oil, and a residual solvent, wherein the essential oil and residual solvent can be an essential oil enriched solvent that is then separated into an essential oil and a residual solvent. Accordingly, the solvent, such as ethyl acetate if used, containing all of the 4-HBITC can be separated from the wet mustard filter cake and can then be further separated as described hereinafter to produce the essential oil. This separation can be achieved by any separation technique as known in the art. For example, such separation techniques can include centrifugation or filtration. In some embodiments, filtration, batch, or continuous centrifugation can be performed.

In one embodiment, the separation can be performed immediately following the reaction described above. In another embodiment, the separation can be performed within about 1 hour following the reaction. In another embodiment, the separation can be performed with about 2 hours following the reaction.

In one embodiment, filtration can be performed within an enclosed filtration system. Such an enclosed filtration system can be used because ethyl acetate is volatile and generally should be contained so as to minimize evaporation into the atmosphere. Filters that contain the filter cake within an enclosed container can also be used because of the volatile nature of ethyl acetate. Some embodiments include vertical and horizontal leaf filters, nutsche filters, candle filters, and filters of similar design where filtration can be achieved within a closed or contained environment.

In another embodiment, centrifugation can be performed.

In one embodiment, the wetted mustard slurry prior to separation can have from about 30% to about 39% removable solid (suspended solids) material. In one embodiment, the wetted mustard slurry prior to separation can have from about 32% to about 35% removable solid (suspended solids) material. In one embodiment, the wetted mustard slurry prior to separation can have from about 33% to about 34% removable solid (suspended solids) material. At this level of solids, one embodiment of separation can include a decanter centrifuge. Decanter centrifuges can comprise a rotating cylindrical horizontal bowl that has a cylindrical section at one end and a radially sloping conical section at the other end with an optional lesser sloping section in between the two sections described above. A scroll can be integrated in the conical section of the bowl and can be driven separately. The wet mustard and solvent mixture (the wet mustard slurry) can enter the separating space through a centrally arranged feed tube entering through the cylindrical section of the bowl. The wet mustard slurry can be spun against the inner bowl wall under the action of centrifugal force. The scroll, which can rotate at a different speed than the bowl shell, can transport the separated mustard solids to the bowl cone where the solids can discharge at the end of the bowl through a discharge port. The ethyl acetate solvent stream can also be simultaneously separated and can exit the decanter at the cylindrical end. The discharged wet mustard solids can drop directly onto a continuous belt dryer operating at a slight vacuum. The temperature within the dryer can be kept at from about 70° C. to about 75° C. so that the ethyl acetate followed by the water evaporates from the wet mustard. The slight vacuum can create a sufficient draft to force the ethyl acetate vapor and water vapor to move towards the vacuum source. The output vapor containing the ethyl acetate vapor and water vapor can both be impinged on a cooling coil that condenses both the vapors to their liquid forms. The condensed liquids can be pumped away to a separating tank where the ethyl acetate and water are separated. Ethyl acetate can be recycled to extract the next lot of mustard seed. The wet mustard can be dried and desolventized completely in this vacuum dryer.

In one embodiment, the wet mustard cake can be separated into a deheated and defatted mustard flour, as described herein, and a residual solvent. The mustard flour can be used as described herein.

In one embodiment, after centrifuging out the residual wet mustard cake, the ethyl acetate can be dried over a drying agent such as anhydrous sodium sulfate to remove the residual water, before evaporation. However, in another embodiment, it has been found that since ethyl acetate forms an azeotrope with about 8% water with a resultant drop in the boiling point of about 8° C., direct evaporation of the moist ethyl acetate results in WMEO without the formation of a water layer.

With this separation technique, the mustard solids can be separated from the solvent stream. The solvent stream can then comprise an enriched solution of WMEO comprising 4-HBITC in solvent, such as ethyl acetate, and can then be stored in a tank prior to evaporation into an essential oil and a residual solvent.

iv. Further Separation

Accordingly, in one embodiment, further separation of the solvent, such as ethyl acetate, from the solvent stream can be performed to yield a residual solvent and an essential oil comprising WMEO comprising 4-HBITC. In one embodiment, evaporation can be performed under reduced pressure and temperature to avert the deleterious thermal effects on WMEO. Several types of vacuum evaporation can be used. In one embodiment, the evaporation can remove about 99% or more of the ethyl acetate in a single pass via the evaporator and thus minimization of the thermal degradation effects on WMEO and hence 4-HBITC can occur. A range of evaporators can be used for this purpose. Rising film evaporators, falling film evaporators, centrifugal evaporators are evaporators that can be used.

Accordingly, in one embodiment, this evaporation can result in an essential oil. In one embodiment, white mustard essential oil (WMEO) comprising from about 5% to about 35% 4-hydroxybenzyl isothiocyanate (4-HBITC) is provided. In other embodiments, WMEO comprising from about 10% to about 30% 4-HBITC is produced. In other embodiments, WMEO comprising from about 15% to about 27% 4-HBITC is produced. In other embodiments, WMEO comprising from about 22% to about 28% 4-HBITC is produced.

v. Further Enrichment

In one embodiment, further enrichment of the 4-HBITC in the white mustard essential oil can occur. In some embodiments, the need may exist to enrich and thus clean up the white mustard essential oil for applications requiring a higher flavor quality. To support these applications, the WMEO can be further purified by first mixing it with hexane, heptane, or methyl pentane at a ratio of one part WMEO to about 1.2 to about 1.3 parts hexane, heptane, or methyl pentane. Such mixing can remove some of the triglyceride materials in the WMEO and can result in separating the lower oil layer containing most of the 4-HBITC from the hexane. This extraction can be repeated one to two or more times to ensure that the WMEO is further enriched. The hexane layers can then be pooled and repeatedly extracted with absolute methanol to remove the 4-HBITC in the hexane layer. The methanol layers and the original lower oil layer can then combined and evaporated under reduced pressure to yield a highly enriched WMEO with from about 30% to about 80% 4-HBITC, by weight. The highly enriched WMEO can comprise from about 35% to about 75% 4-HBITC, by weight. The highly enriched WMEO can comprise from about 45% to about 70% 4-HBITC, by weight. The highly enriched WMEO can comprise from about 49% to about 65% 4-HBITC, by weight. The highly enriched WMEO can comprise from about 45% to about 55% 4-HBITC, by weight. The highly enriched WMEO can comprise from about 35% to about 80% 4-HBITC, by weight. The highly enriched WMEO can comprise from about 40% to about 80% 4-HBITC, by weight. The highly enriched WMEO can comprise from about 45% to about 80% 4-HBITC, by weight. The highly enriched WMEO can comprise from about 50% to about 80% 4-HBITC, by weight. This highly purified WMEO can then be suitable for addition to food and beverage products requiring a higher flavor quality. In another embodiment, to make for easy dispensing and to ensure greater stability, the WMEO can then be mixed at a suitable ratio with a water soluble hygroscopic substance such as maltodextrin. Because the WMEO is now enriched in 4-HBITC, the ratio of WMEO to maltodextrin is less than 1:9. In one embodiment, the range can be from about 1:6 to about 1:9.

The essential oil itself, which contains one or more moisture sensitive isothiocyanate compounds, preferably 4-hydroxybenzyl isothiocyanate, may then be utilized in the compositions and methods as described in, for example, U.S. Pat. No. 6,361,812B1; U.S. Pat. No. 6,558,723B2; U.S. Pat. No. 7,105,190B2 and U.S. Pat. No. 7,658,961.

vi. Further Processes

As described in the references herein, additional processing can be performed to the WMEO and/or the 4-HBITC. In one embodiment, freezing of the WMEO can be performed. Such freezing can preserve the essential oil. Freezing can be performed down to about −25° C. After freezing, the WMEO can be plated into maltodextrin, or any other hygroscopic carrier, and used as described in, for example, U.S. Pat. No. 6,361,812B1; U.S. Pat. No. 6,558,723B2; U.S. Pat. No. 7,105,190B2 and U.S. Pat. No. 7,658,961.

III. Antimicrobial Efficacy

The concentration of 4-hydroxybenzyl isothiocyanate in white mustard essential oil is dependent on the fat content of the starting partially defatted white mustard press cake. This property holds because the solvent dissolves all fat soluble materials from the resulting moist mustard flour, and the composition of the white mustard essential oil is the sum total of the 4-hydroxybenzyl isothiocyanate and the residual fat soluble material in the starting partially defatted white mustard press cake. For example, if whole mustard seed without any defatting and having an initial fat content of about 26-28% is used as the starting material, the concentration of 4-HBITC in WMEO is about 5-6%; when partially defatted white mustard powder with a fat content of about 17.5% is used as the starting material the concentration of 4-HBITC in WMEO is about 10.1%; when the fat content is about 14% in the starting partially defatted white mustard the concentration of 4-HBITC in WMEO is about 15.5-15.9%; when the fat content of the starting defatted white mustard is about 8.2%, the concentration of 4-HBITC is about 24% in the resulting WMEO; finally when the fat content is about 6-7% in the starting partially defatted white mustard, the 4-HBITC concentration in WMEO is about 26%. Not wishing to be bound by theory, the fat content in the starting partially defatted white mustard is approximately linearly correlated to the concentration of 4-HBITC in WMEO. If the starting white mustard press cake is fully defatted then the concentration of 4-HBITC in WMEO can reach as high as about 90%. The inventors have surprisingly found that the range of antimicrobial effectiveness of WMEO is dependent on the concentration of 4-hydroxybenzyl isothiocyanate in it. For example, WMEO, with a 4-hyroxybenxzyl isothiocyanate concentration of about 5-6%, can be effective against gram negative organisms only and has been found to have substantially no effect on the growth of gram positive organisms. When the 4-hydroxybenzyl isothiocyanate concentration in WMEO is at about 15%, a noticeable but limited inhibitory effect against gram positive organisms in addition to the sustained inhibitory effect on gram negative organisms has been observed. When the 4-hydroxybenzyl isothiocyanate concentration in WMEO is at about 24%, a very noticeable inhibitory effect against both gram negative and gram positive organisms has been observed.

Not wishing to be bound by theory, the inventors think that the presence of fixed mustard oil along with 4-HBITC in the WMEO exerts a partitioning effect on the 4-HBITC, which can slow or prevent its release into the aqueous media, which is required for action against microorganisms. Gram negative microorganisms have a cell wall composed of lipo-polysaccharides while gram positive microorganisms have a cell wall composed mostly of peptidoglycan type molecules. With the higher presence of lipids in the lipo-polysaccharide type structures, the inventors think that hydrophobic compounds, such as 4-HBITC, will be closely associated with such structures while the absence of lipids in the peptidoglycan type structures promotes less of such an association.

Thus, further enrichment and clean up of white mustard essential oil having a lower concentration of 4-HBITC can be performed to both enhance its range of activity and also for applications requiring a higher flavor quality. To support these applications, the WMEO can be further purified by first mixing it with hexane or methyl pentane at a ratio of 1 part WMEO to about 1.2 to about 1.3 parts hexane or methyl pentane, to remove some of the triglyceride materials in the WMEO, and separating the lower oil layer containing most of the 4-HBITC from the hexane. This extraction can be repeated one to two more times to ensure that the WMEO is further enriched. The hexane layers can then pooled and repeatedly extracted with absolute methanol to remove the 4-HBITC in the hexane layer. The methanol layers and the original lower oil layer is then combined and evaporated under reduced pressure to yield a highly enriched WMEO with greater than 50% 4-HBITC. This highly purified WMEO is suitable for addition to food and beverage products requiring a higher flavor quality. To make for easy dispensing and to ensure greater stability, the WMEO can then mixed at a suitable ratio with a water soluble hygroscopic substance such as maltodextrin. Because the WMEO is now enriched in 4-HBITC the ratio of WMEO to maltodextrin can be less than about 1:9.

IV. Flour

The resulting dried, deheated, and defatted mustard flour can have a protein content of about 42%, or from about 35% to about 45%, or from about 35% to about 45%, or from about 38% to about 43%. The flour can have a fat content of about 2.5%, or from about 1% to about 5%, and from about 2% to about 4%. The mustard seed mucilage having emulsification properties is not altered as a result of processing to remove the white mustard essential oil and the resulting deheated and defatted mustard flour can be used for the original intended purpose as an emulsifier for meat products, with the additional benefit of being low in fat. Unlike the thermally deheated mustard flour that still has the intact sinalbin precursor, which in contact with a glucohydrolase enzyme coming from another source in the food supply can generate undesirable "heat", the deheated and defatted mustard flour as disclosed herein will not generate any of the "heat" when contacted with other foods sources. Additionally, the high protein content of the deheated & defatted mustard flour can lend itself to other uses as a protein source in protein enriched products. Prior approaches to making use of mustard protein have to do with extracting the protein component out of the mustard seed with the use of various solutions, thus decoupling the emulsification property from the protein component. The approach described herein allows the flexibility for a food processor to make use of the whole deheated & defatted mustard or of the protein separately without the risk of generating objectionable "heat" by accidental activation of the myrosinase system.

Accordingly, one embodiment of the present invention relates to a deheated and defatted mustard flour. After drying the wet mustard press cake resulting from the separation step above, defatted and deheated mustard flour is formed in good yield. This deheated and defatted mustard flour has no sinalbin present as all of it has been hydrolyzed to 4-hydroxybenzyl isothiocyanate and the myrosinase enzyme is largely denatured as a result of the drying step. Accordingly, one embodiment includes a deheated and defatted mustard flour. The deheated and defatted mustard flour can be substantially free of sinalbin, and/or substantially all of the myrosinase enzyme can be denatured. The emulsification properties associated with mustard flour to do with its mucilage is well preserved in the deheated & defatted mustard flour. The resulting deheated and defatted mustard flour can have a protein content of about 42%, or from about 35% to about 45%, or from about 35% to about 45%, or from about 38% to about 43%. The flour can have a fat content of about 2.5%, or from about 1% to about 5%, and from about 2% to about 4%. Because the deheated and defatted mustard flour is substantially devoid of sinalbin and/or the myrosinase enzyme has been denatured, the heat sensation associated with wetted mustard flour will not arise. Thus, the mustard flour can be used in many situations requiring an emulsifier or a high protein component. For example, the flour can be used as a replacer of currently used mustard flour. Specific examples include in meat emulsions, such as sausages; as a high protein source similar to soy and canola meal in high protein bar type products; and in pet foods as a high protein component. Presence of relatively large amounts of the sulfur amino acids such as cystine and methionine and lysine, which are not found well distributed in the plant kingdom, should add to the quality of the protein component. Finally this deheated and defatted mustard flour can be quite economical considering that several high value components are derived from it.

IV. Test Method for Measurement of 4-Hydroxybenzyl Isothiocyanate and Identification of Moisture sensitive Isothiocyanate Compounds Supercritical fluid chromatography can be used to determine the amount of 4-hydroxybenzyl isothiocyanate in a preservative composition. First an accurately weighed amount of the preservative composition is either dissolved in a compatible solvent such as ethyl acetate or ethyl acetate and ethanol mixtures or solid preservative compositions are extracted repeatedly with ethyl acetate.

These solutions are analyzed by supercritical fluid chromatography using the method described by Buskov, S. et al., "Supercritical fluid chromatography as a method of analysis for the determination of 4-hydroxybenzylglucosinolate degradation products," Journal of Biochemical and Biophysical Methods, Vol. 43, pp 157-174 (2000) with the following modifications. A Berger SFC 3D system equipped with a photodiode array detector (Berger Instruments Inc., Newark, Del.) is used for the analysis. An ethyl acetate solution (10 µl) containing butyl paraben as the internal standard is injected onto a Cyano column (15 cm×5 mm i.d., 5 µm particle size, Phenomenex, Torrance, Calif.). The oven temperature is 50° C. The mobile phase is $CO_2$ with 4% MeOH as a modifier maintained at a pressure of 200 Bar and pumped at 2 mL/min. The eluate is detected at 226 and 252 nm. The 4-hydroxybenzyl-isothiocyanate elutes after about 3.8 min. Its identity is confirmed by chromatographing a pure sample of synthetic 4-hydroxybenzyl isothiocyanate prepared in the following manner.

The method described by Soledade, M., Pedras, C. and Smith, K. C. entitled "Sinalexin, phytoalexin from whole mustard elicited by destrucin B and *Alternaria brassicane*" in Phytochemistry, 46(5), p. 833-837, 1997 was modified and is used as follows. In a 100 mL round bottom flask, thiophosgen (1.1 g, 9.56 mmol) is dissolved in chloroform (20 mL). Subsequently, a solution of p-hydroxybenzylamine (400 mg, 3.25 mmol) and triethyl amine (820 mg, 8.1 mmol) dissolved in methanol (20 mL) is added dropwise to the stirred solution kept at 0-4° C. using an ice bath. After approximately 30 min, addition is finished and the mixture allowed to remain in the ice bath for an additional 10 minutes. The reaction is followed by Thin Layer Chromatography on silica gel $60_{254}$ using the FCC eluent as the mobile phase. Subsequently, the solvent is removed in vacuum by rotary evaporation at 45° C. and the residue is dissolved in a mixture of dichloromethane-ethyl acetate (49+1; 4 mL). The compound is further purified by flash column chromatography as described by Still, W. C., Kahn, M. and Mitra A. J. in "Rapid chromatographic method for separation with moderate resolution," Organic Chemistry, 14, pp. 2923-2925. 1978, with modifications. After flushing the column with mobile phase, the reaction product dissolved in mobile phase (4 mL) is placed on top of the column. Elution is performed by adjusting the argon overpressure in a way so that the solvent head drops about 2 inch/min. Aliquots of 10 mL are collected. The target compound usually elutes in fractions 6-10. The fractions are combined and after removing the solvent by rotary evaporation at 45° C. in vacuum, a yellow oil is obtained (typical yield: 66%). The structure of 4-hydroxybenzyl isothiocyanate is confirmed by $H^1$-NMR in $CDCl_3$, $C^{13}$-NMR in $CDCl_3$ and GC-MS operating in electron impact mode.

Moisture sensitive isothiocyanate compounds are identified by suspending the isothiocyanate containing material in an aqueous phosphate buffer (pH of about 3.6) at room temperature. The resulting suspension is shaken well, and a time zero sample is withdrawn into a separatory funnel and extracted with ethyl acetate. This extraction is repeated with two further volumes of ethyl acetate. The separated ethyl acetate layers are pooled and dried over anhydrous sodium sulfate and kept frozen before analysis of the time zero isothiocyanate concentration by supercritical fluid chromatography. To determine sensitivity of the isothiocyanate compound to hydrolytic degradation, the isothiocyanate suspension is stored at a temperature between about 20° C. to about 23° C. for a period of about 24 hours. The extraction procedure is repeated after 24 hours and the level of residual isothiocyanate compound is measured by supercritical fluid chromatography. Moisture sensitive isothiocyanate compounds are characterized by at least about a 20% reduction in concentration of the isothiocyanate after about 24 hours, relative to the time zero or starting concentration.

VI. Examples

Example 1

A white mustard essential oil is generated by adding water to ground white mustard seeds and then extracting the essential oil with supercritical carbon dioxide according to the known processes described in the art. Immediately after extraction, residual moisture is removed from the essential oil by centrifugation and by drying under vacuum. The resulting white mustard essential oil contains about 25% by weight 4-hydroxybenzyl isothiocyanate. The essential oil is suspended in an aqueous phosphate buffer (pH of about 3.6) at room temperature (about 20-23° C.) and the level of 4-hydroxybenzyl isothiocyanate measured at time zero and after about 24 hours of storage as described in the preceding section. The percent reduction in level of 4-hydroxybenzyl isothiocyanate after 24 hours is about 72%. Therefore, 4-hydroxybenzyl isothiocyanate is a moisture sensitive isothiocyanate compound.

Example 2

White mustard essential oil was prepared by first cold pressing 800 kg of white mustard seed using a Rosedowns Mini 200 screw press unit. The resulting press cake exited the press at about 75-78° C. and was immediately cooled to room temperature by hammer milling. The oil content of the press cake was 17%. About 340 kg from the hammer milled white mustard press cake was introduced into a ribbon blender and 78 g ascorbic acid added to it while blending to ensure uniform mixing. About 102 kg of tap water at room temperature was added in small proportions to ensure uniform wetting of the press cake. After mixing for about 10-15 minutes, the moistened and myrosinase enzyme activated press cake was transferred to a stirred solvent tank containing 626 kg ethyl acetate. The moistened, activated mustard press cake and ethyl acetate slurry was stirred within the closed solvent tank for about 4 hours at room temperature, to ensure generation and transfer of the 4-hydroxy benzyl isothiocyanate from the moist white mustard press cake into the ethyl acetate.

At the end of the reaction period the slurry of moist white mustard press cake in ethyl acetate was pumped into a decanter centrifuge to separate the ethyl acetate from the moist white mustard press cake. The ethyl acetate layer was collected in a static solvent tank while the wet white mustard press cake with some residual ethyl acetate was directly transferred into a vacuum assisted belt dryer. The vacuum conditions allowed the moist ethyl acetate to leave the mustard press cake and get condensed in an external condenser. The ethyl acetate top layer was separated out and stored for re-use while the water layer was discharged. The mustard press cake continued to travel on a continuous belt towards the bottom of the dryer where the dried, solvent free mustard press cake exited via a screw conveyor. This deheated and defatted mustard flour was analyzed for its gross composition and its amino acid composition. The ethyl acetate layer containing the WMEO was pumped into a rising film evaporator kept under about 56 cm Hg vacuum to remove the ethyl acetate from the white mustard essential oil. The evaporation step resulted in about 65.5 kg of WMEO containing 8.4% 4-hydroxybenzyl isothiocyanate.

Example 3

White mustard essential oil was prepared by first cold pressing 5 kg of white mustard seed using a model KK8 single screw press (KERNKRAFT, Moosbauer and Rieglsperger GbR. Germany) to yield a white mustard press cake with 6.8% fixed oil and a temperature of about 60° C. The press cake was hammer milled to provide a uniform powder and 151.5 g of the powder weighed out into a weighing pan. In a closed mixing vessel equipped with a top drive mixer 45.5 g of tap water was mixed with 305 mL of ethyl acetate and 0.036 g of ascorbic acid added while mixing. Immediately after adding the ascorbic acid, the partially defatted mustard powder in the weighing pan was added to the mixing vessel and mixed at high speed to ensure uniform dispersion. When a uniform slurry had formed the speed was slowed down and the mixing continued for a further 4 hours. The slurry was removed from the mixing vessel at that time and centrifuged to separate the ethyl acetate from the moistened, partially defatted mustard press cake. The ethyl acetate was decanted from the centrifuge tubes and evaporated under reduced pressure to yield about 9.5 g white mustard essential oil containing 27% 4-hydroxybenzyl isothiocyanate.

Example 4

A powdered preservative composition is prepared by triturating the white mustard essential oil of Example 2 with maltodextrin according to the following formulation.

|  | Wt % | Weight |
| --- | --- | --- |
| White mustard essential oil (from Example 2) | 10.0% | 10.0 g |
| Maltodextrin (15 DE) | 90.0% | 90.0 g |
| TOTAL | 100% | 100 g |

The blend of materials is intimately mixed or triturated using a mortar and pestle. The level of 4-hydroxybenzyl isothiocyanate in the resulting preservative composition is about 0.84% by weight. The level of 4-hydroxybenzyl isothiocyanate in the powdered preservative composition remains stable during storage of the preservative composition at room temperature (about 21.1° C.).

Example 5

A powdered preservative composition is prepared by triturating the white mustard essential oil of Example 3 with maltodextrin according to the following formulation.

|  | Wt % | Weight |
| --- | --- | --- |
| White mustard essential oil (from Example 2) | 10.0% | 10.0 g |
| Maltodextrin (15 DE) | 90.0% | 90.0 g |
| TOTAL | 100% | 100 g |

The blend of materials is intimately mixed or triturated using a mortar and pestle. The level of 4-hydroxybenzyl isothiocyanate in the resulting preservative composition is about 2.6% by weight. The level of 4-hydroxybenzyl isothiocyanate in the powdered preservative composition remains stable during storage of the preservative composition at room temperature (about 21.1° C.).

Example 6

Peptone broth (0.5% by weight, pH 7.1) was inoculated with 20-24 hour old cultures of *Staphylococcus aureus* (ATCC 6538), *Salmonella enteritidis* (ATCC 13076), *Listeria monocytogenes* (ATCC 7644) grown on trypticase soy agar slants (incubated at 35° C.) and *Clostridium perfringens* (ATCC 3624) cultures grown on Shahidi Ferguson perfringens (SFP) agar slants incubated under anaerobic conditions at 35° C. Starting counts were between $1 \times 10^5$ and $1 \times 10^7$ cfu $mL^{-1}$. The powdered preservative composition of Example 4 was introduced into the inoculated media to reach a starting 4-HBITC level of 350 mg $L^{-1}$ and shaken well. Samples were stored at 6.5° C. and plated on microbial content test (MCT) agar at 1 day after neutralization with Letheen as per USP 26 (United States Pharmacopoeia, Rockville, Md., USA). The mean log reductions in microbial counts were 2.23 for *S. aureus*, 1.61 for *S. enteritidis*, 0.80 for *L. monocytogenes* and 2.17 for *C. perfringens*.

Example 7

Peptone broth (0.5% by weight, pH 7.1) was inoculated with 20-24 hour old trypticase soy agar slants (incubated at 35° C.) of *Staphylococcus aureus* (ATCC 6538), *Salmonella enteritidis* (ATCC 13076), *Listeria monocytogenes* (ATCC 7644). *Clostridium perfringens* (ATCC 3624) cultures were grown on Shahidi Ferguson perfringens (SFP) agar slants and incubated under anaerobic conditions at 35° C. Starting counts were between $1 \times 10^5 \sim 1 \times 10^7$ cfu $mL^{-1}$. The powdered preservative composition of Example 5 was introduced into the inoculated media to reach a starting 4-HBITC level of 360 mg $L^{-1}$ and shaken well. Samples were stored at 6.5° C. and plated on microbial content test (MCT) agar at 1 day after neutralization with Letheen as per USP 26 (United States Pharmacopoeia, Rockville, Md., USA). The mean log reductions in microbial counts were 3.95 for *S. aureus*, 4.93 for *S. enteritidis*, 4.17 for *L. monocytogenes* and 5.40 for *C. perfringens*.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A process for producing white mustard seed essential oil, having antimicrobial activity against gram positive and gram negative microorganisms, said process comprising:
    a) Providing mustard seed comprising a precursor sinalbin and myrosinase enzyme, wherein the mustard seed comprises a fixed oil;
    b) Reducing the fixed oil content of the mustard seed by mechanical expression of said seed conducted at a temperature less than about 50° C. to provide reduced oil mustard seed comprising from about 2% to about 8.2% of fixed oil, by weight of the reduced oil mustard seed;
    c) Reducing the particle size of the reduced oil mustard seed to produce a mustard powder;
    d) Activating the myrosinase enzyme in the mustard powder by using a water solvent, a cellulase enzyme and ascorbic acid at a concentration from about 0.75 millimole to about 3 millimole to form a slurry, wherein the myrosinase enzyme catalyzes the production of an essential oil comprising an isothiocyanate from the sinalbin precursor and wherein the water solvent comprises ethyl acetate and water at a ratio of mustard to water to ethyl acetate of from about 1:0.25:1.5 to about 1:0.5:3, by weight;
    e) Separating the slurry into white mustard seed essential oil, said oil comprising from about 24% to about 35% 4-hydroxybenzyl isothiocyanate, and a residual solvent by centrifugation.

* * * * *